US012642989B2

(12) United States Patent
Fella et al.

(10) Patent No.: US 12,642,989 B2
(45) Date of Patent: Jun. 2, 2026

(54) SYSTEM FOR GENERATING LIGHT RADIATION TO NEUTRALIZE MICROORGANISMS

(71) Applicant: LEONARDO—SOCIETA' PER AZIONI, Rome (IT)

(72) Inventors: Paolo Fella, Rome (IT); Eugenio Fazio, Rome (IT)

(73) Assignee: Leonardo—Societa' per Azioni, Rome (IT)

( * ) Notice: Subject to any disclaimer, the term of this patent is extended or adjusted under 35 U.S.C. 154(b) by 355 days.

(21) Appl. No.: 18/574,278

(22) PCT Filed: Jul. 11, 2022

(86) PCT No.: PCT/IT2022/050201
§ 371 (c)(1),
(2) Date: Dec. 26, 2023

(87) PCT Pub. No.: WO2023/286096
PCT Pub. Date: Jan. 19, 2023

(65) Prior Publication Data
US 2024/0350826 A1     Oct. 24, 2024

(30) Foreign Application Priority Data
Jul. 12, 2021   (IT) ........................ 102021000018290

(51) Int. Cl.
*A61N 5/06*         (2006.01)
(52) U.S. Cl.
CPC ......... *A61N 5/0624* (2013.01); *A61N 5/0603* (2013.01); *A61N 2005/0604* (2013.01);
(Continued)

(58) Field of Classification Search
CPC ................ A61N 5/0624; A61N 5/0603; A61N 2005/0604; A61N 2005/0609;
(Continued)

(56) References Cited

U.S. PATENT DOCUMENTS

| | | | |
|---|---|---|---|
| 10,413,626 | B1 | 9/2019 | Barron et al. |
| 2017/0030555 | A1 | 2/2017 | Lalicki et al. |
| 2018/0164221 | A1 | 6/2018 | Singh et al. |

FOREIGN PATENT DOCUMENTS

| | | |
|---|---|---|
| KR | 2019 0090665 | 8/2019 |

OTHER PUBLICATIONS

International Search Report and Written Opinion for International PCT Application No. PCT/IT2022/050201 mailed Oct. 31, 2022 in 9 pages.

*Primary Examiner* — Jonathan T Kuo
(74) *Attorney, Agent, or Firm* — Knobbe, Martens, Olson & Bear, LLP

(57) ABSTRACT

A system for generating light radiation to neutralize microorganisms comprises a light source for emitting a light radiation, storage means with one or more unique identification codes, each of which is associated with a respective microorganism, and at least one respective wavelength range associated with said microorganism, and a logic control unit. The logic control unit is configured to select a wavelength range based on the microorganism to be neutralized, activate the light source in such a way that light radiation emitted by said light source has a wavelength within said selected wavelength range, so that, when the system is in use, the light radiation induces optical resonance in the microorganism, causing denaturation of genetic patrimony of the microorganism.

23 Claims, 7 Drawing Sheets

(52) U.S. Cl.
CPC ................. *A61N 2005/0609* (2013.01); *A61N 2005/0651* (2013.01); *A61N 2005/0654* (2013.01); *A61N 2005/0659* (2013.01); *A61N 2005/0661* (2013.01); *A61N 2005/0663* (2013.01); *A61N 2005/0667* (2013.01)

(58) Field of Classification Search
CPC .... A61N 2005/0651; A61N 2005/0654; A61N 2005/0659; A61N 2005/0661; A61N 2005/0663; A61N 2005/0667; A61N 5/06–2005/073; A61B 1/0638; A61B 1/267; A61B 1/2736; A61L 2103/05; A61L 2103/09; A61L 2103/75; A61L 2/084; A61L 2/085; A61L 2202/11; A61L 2/24; A61L 2/10; A61L 2/00–2/28; Y02A 50/30

See application file for complete search history.

Fig. 10A                    Fig. 10B

SYSTEM FOR GENERATING LIGHT RADIATION TO NEUTRALIZE MICROORGANISMS

CROSS-REFERENCE TO RELATED APPLICATIONS

The present application claims the priority of PCT application No. PCT/IT2022/050201, filed Jul. 11, 2022, which claims the priority of Italian application No. IT102021000018290, filed Jul. 12, 2021, the disclosures of which are incorporated by reference herein in their entireties.

BACKGROUND

Technical Field

The present application relates to a system for generating light radiation to neutralize microorganisms.

The term "microorganisms" refers to both bacteria and viruses, but also to any pathogen, such as fungi, algae, spores, toxins, proteins, helminths, etc.

In particular, the present application relates to also the structure of a system configured to generate a light radiation with technical characteristics (such as weight length) such as to inhibit microorganisms, such as for example bacteria and viruses, in particular the SARS COV-coronavirus 2, through a denaturation of the genetic heritage of the microorganism itself.

The expression "denaturation of the genetic heritage" means the denaturation of at least one nucleic acid (DNA or RNA).

In general, by means of the light radiation generated by the system it is possible to transfer an amount of energy to the microorganism that causes an optical resonance in the microorganism itself.

The optical resonance causes an irreversible physiological and morphological transformation of the microorganism.

In the event that the microorganism is a virus and in particular a SARS COV-2 coronavirus, the light radiation generated by the system causes an irreversible damage to the genetic material of the SARS COV-2 coronavirus.

In the following description, reference will be made to the system used to neutralize any microorganism which is provided with at least one first membrane.

In fact, a microorganism can have a plurality of membranes.

In case a microorganism has a first membrane and a second membrane, the first membrane can be the outer membrane and the second membrane can be the inner membrane, i.e. the second membrane is arranged in the internal volume delimited by the first membrane.

In one example, when the organism is a virus that has two membranes, the first membrane can be the pericapsid and the second membrane can be the capsid.

In a further example, when the organism is a virus that has three membranes, the first membrane is the supercapsid, the second membrane is the pericapsid, and the third membrane is the capsid.

The same system can be used with the same advantages for different purposes.

In a first example, the system can be used to sanitize or sterilize any public or private environment, intended to receive people, such as hospices, hospital wards, operating theatres, laboratories, cinemas, theatres, airplanes, trains, restaurants, bars, discos, gyms, swimming pools, etc.

In a second example, the system can be used to sanitize or sterilize any object, such as an instrument, a product, or any fluid, such as a liquid or gas.

In a third example, the system can be used to sterilize food and drinks, even in an industrial production cycle (for example, sterilization of salmonella, botulin, etc.).

In a further example, said system can be used in the medical field to reduce a local viral load (for example present in the airways and/or in the pulmonary alveoli of a respiratory system and/or in the patient's blood) or to treat dermatological alterations or infected wounds.

DESCRIPTION OF THE RELATED ART

In general, microorganisms are organisms not visible to the human eye.

Said microorganisms contain genetic material, in particular at least one nucleic acid, for example DNA and/or RNA.

Bacteria can be between 0.2 and 10 μm in size and viruses between 0.015-0.25 μm.

As known viruses are microorganisms visible only under the electron microscope.

Furthermore, viruses are not capable of autonomous life, but require the metabolic apparatus of a cell. So a virus to live and replicate is forced to infect another organism.

It is also known that a UV light radiation is able to interact with nucleic acids, DNA and RNA, causing a denaturation of the genetic patrimony.

Consequently, systems capable of emitting a UV light radiation to denature the genetic heritage of microorganisms are known.

If on the one hand, the use of UV light radiation has the advantage of having a germicidal action against viruses or bacteria, on the other hand a disadvantage of using UV light radiation is that this UV light radiation interacts also with human DNA and RNA, so as to be harmful to people who are directly affected by said light radiation, even when the intensity of the light radiation is reduced.

Furthermore, the times of exposure to light radiation to obtain a significant decrease in the viral/bacterial population are sufficiently long.

Consequently, in the case of viruses such as coronaviruses and in particular SARS-COV-2, emitting UV light radiation against these viruses on a human body tissue, would mean not only neutralizing the virus but also damaging said human body tissue, having a toxic-oncological action.

For this reason, i.e. due to the toxic-oncological action of a UV light radiation against a human body tissue, the use of this UV light radiation is prohibited in the presence of people and above all a direct use on the human body is prohibited.

The limits of use of a UV light radiation are stringent: a maximum dose of 30 J/m$^2$, calculated over a time interval of 8 hours.

Furthermore, in the case of the sanitization of surfaces or objects, made up of solid materials or glassy materials, it must be considered that a prolonged UV irradiation time may be capable of causing a structural change in said solid or glassy materials.

Additional systems can generate light radiation in order to sanitize or sterilize to neutralize viruses/bacteria.

These systems are provided with a light source which is a laser and has a wavelength such as to emit a blue or red light radiation that can cause the denaturation of the genetic heritage of microorganisms, as verified empirically but not theoretically.

However, in addition to the laser, it is necessary to use photo-sensitizers or dyes or other substances that are not easy to find and therefore represent a limit of use for the system.

For example, the presence of photo-sensitizers is not necessary to emit blue light when a laser is a pulsed laser at high frequencies (of the order of magnitude of Femtoseconds).

However, a disadvantage is that it is difficult to find and use such a laser.

Furthermore, the use of wavelengths belonging to the visible spectrum or the infrared spectrum to inhibit microorganisms is not known.

An aim of the present application it is to overcome said disadvantages, providing a system configured for emitting a light radiation capable to neutralize said microorganisms, particularly bacteria and viruses, and more particularly the SARS-COV 2 coronavirus, on an object or on a tissue of the human body, without that said tissue of the human body being damaged, when the light radiation is directed towards a person.

In particular, said system is designed to emit UV light radiation with a wavelength included in a narrow band, which allows said UV light radiation to interact with the microorganism and causes an optical resonance capable of neutralizing said microorganism.

On the one hand, an energy transfer from the light radiation to the microorganism allows to neutralize the microorganism and, on the other hand, although this light radiation has a high power density inside the microorganism as it is amplified inside the microorganism by effect of the resonance phenomenon, this light radiation is not harmful to healthy tissue and therefore is not harmful to people's health.

It is therefore object of the present application to provide a system for generating light radiation to neutralize microorganisms.

BRIEF DESCRIPTION OF THE DRAWINGS

FIGS. 10A and 10B are respectively a perspective view of a first smallpox virus model for numerical simulations and a perspective view of a second smallpox virus model for numerical simulations, in which the second virus model has different dimensions from the first model;

DETAILED DESCRIPTION

Figure 1:
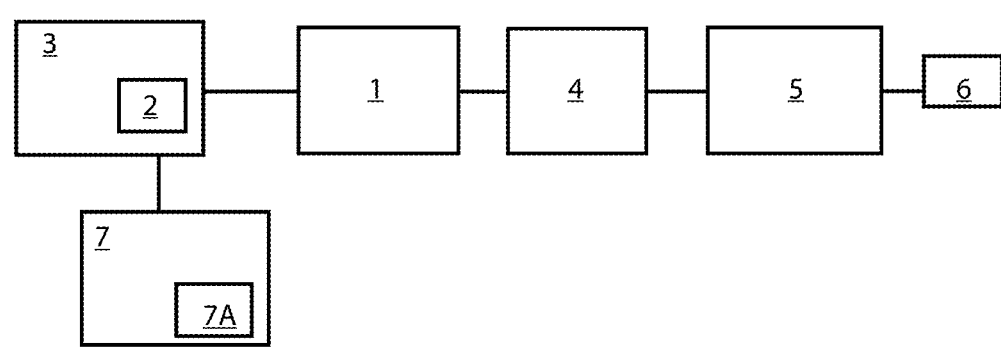
FIG. 1 is a schematic view of the system, according to the present application.
Figure 2A:
FIG. 2A is a schematic view showing a microorganism, represented by a sphere, and a light radiation, represented by a sine wave, in which the light radiation is generated by the system of FIG. 1 and is about to hit the microorganism.
Figure 2B:
FIG. 2B is a schematic view showing the microorganism in which the light radiation has been partially trapped, due to an optical resonance, and this light radiation bounces from a portion of the internal wall of the microorganism to another portion of the same internal wall, so that the intensity of light radiation increases and a quantity of energy is transferred in the form of heat on this internal wall, while a further light radiation is about to hit the microorganism.
Figure 2C:
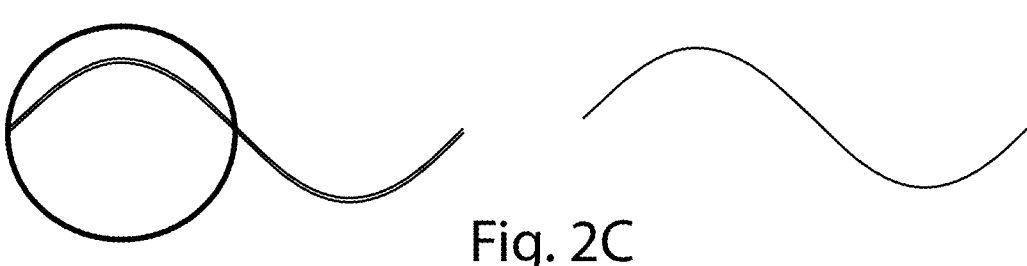
FIG. 2C is a schematic view showing the microorganism in which said further light radiation is partially trapped, while a further light radiation is about to hit the microorganism, so that the intensity of light radiation inside the membrane continues to increase and a quantity of energy transferred in the form of heat on the inner wall of the microorganism increases.

With reference to FIG. 1, a system for generating light radiation to neutralize microorganisms, in particular the SARS COV-2 coronavirus.

Said system comprises:
   a light source 1 for emitting a light radiation,
   storage means 2, in which the following are stored:
      one or more unique identification codes, each of which is associated with a respective microorganism, and
      at least one respective wavelength range associated with said microorganism,
   a logic control unit 3, connected to said light source 1 and to said storage means 2, and configured to:
      select a wavelength range based on the microorganism to be neutralized, activate said light source 1 in such a way that the light radiation emitted by said light source 1 has a wavelength within said selected wavelength range, so that, when the system is in use, said light radiation induces an optical resonance in the microorganism, causing a denaturation of the genetic patrimony of said microorganism.

With reference to the light source 1, said light source can be a UV lamp or a LED light source or a laser.

Particularly, said wavelength ranges were previously identified for each microorganism, such a way as to induce an optical resonance phenomenon within said microorganism, as better disclosed below.

A plurality of wavelength ranges can be associated with one or more microorganisms.

The values of the wavelengths of such wavelength ranges are chosen such a way as to induce an optical resonance within said microorganism.

When a plurality of wavelength ranges is associated with a microorganism, said logic control unit 3 can be configured to select a wavelength range between said plurality of wavelength ranges.

It is preferable that the logic control unit is configured to select the wavelength range whose wavelength values are greater than the wavelength values belonging to the other wavelength ranges of said plurality of wavelengths.

In fact, a light radiation with a higher wavelength value may belong to the visible spectrum rather than the ultraviolet spectrum.

Therefore, the light radiation that radiates the microorganism is not harmful to human tissues.

It is preferable that the light source 1 is an LED light source since it is capable of emitting a light radiation having a narrower band than the light radiation emitted by a UV lamp and with a limited emission angle.

It is preferable that said bandwidth is less than or equal to 4 nm and it is further preferable that it is between 1 nm and 3 nm.

Advantageously, using a narrow bandwidth, in particular between 1 nm and 3 nm, it is possible to ensure on the one hand that the total dose of light radiation to which the patient is exposed is lower than the safety limits, and on the other hand that the microorganism is irradiated with a light radiation having a wavelength such as to induce said optical resonance.

In regards to the light radiation emitted by an LED light source, the bandwidth and the limited emission angle help to have a light radiation capable of having a greater sterilization or sanitization capacity.

In particular, the fact that the light radiation has a limited emission angle allows the light radiation to maintain a high power density even at a significant distance from the light source.

Furthermore, an LED light source consumes less energy than a UV lamp to emit light radiation with the same intensity.

From an energy point of view, it is further preferable that said light source 1 is a laser.

Therefore, the laser can be used to efficiently neutralize a microorganism belonging to the virus family called Coronaviridae, such as the SARS-COV-2 coronavirus.

Said system can comprise at least one optical device 4 for focusing the light radiation emitted by the light source 1 on a human tissue or on an object to be sterilized or sanitized.

Said optical device 4 is connected to the light source 1 through at least one first optical fibre.

Said optical device 4 can comprise one or more lenses.

Said one or more lenses can be convergent to decrease the diameter of the light radiation emitted by the light source 1 or divergent to increase the diameter of the light radiation emitted by the light source 1.

The system can comprise a plurality of optical devices, even different from each other, depending on the type of light source.

The system can comprise filtering means 5 for selecting a predetermined bandwidth so as to obtain an optical resonance in the microorganism.

Said filtering means are necessary when the light source is a UV lamp or an LED light source, while when the light source is a laser the presence of said filtering means is not necessary.

Said filtering means 5 can comprise a band-pass filter.

In the embodiment being disclosed, said optical device 4 is arranged between said light source 1 and said filtering means 5.

However, said filtering means 5 can be positioned elsewhere.

For example, said filtering means 5 can also be included in the optical device 4.

In fact, the light source 1 may be capable of emitting a light radiation having a broadband spectrum, comprising a plurality of wavelengths, and the filtering means 5 may comprise or consist of a band-pass filter configured to allow only the passage of wavelengths in a wavelength range.

As already mentioned, the bandwidth of the wavelength range is preferably less than or equal to 4 nm, more preferably between 1 nm and 3 nm.

The system can comprise an optical probe 6.

Said optical probe 6 can be connected to the filtering means 5, if said filtering means 5 are included in the system, or to the optical device 4, if said filtering means 5 are not included in the system (for example when the light source is a laser).

In particular, said optical probe 6 can be connected to the filtering means 5 or to said optical device 4 through a second optical fibre.

In a variant, the light radiation 1 can be included in said optical probe 6.

The optical probe can be a probe of a bronchoscope or a laryngopharyngeal probe or a gastroesophageal probe or an endoscopic probe.

Regardless of the type of probe mentioned above, the optical probe 6 is to be inserted in use in a patient, for example inside the airways, esophagus, hollow organs and/or blood vessels.

Regardless of the presence of the optical probe 6, the system can include a user interface module 7.

Said user interface module 7 can comprise a display device 7A to display the light radiation and one or more parameters associated with said light radiation, for example the wavelength, the optical power, the duration of the irradiation.

The system described above can be included in a dialyzer machine.

In general, a hemodialysis machine comprises:

at least one dialyzer filter, and a hydraulic circuit to be connected to a first vascular access point of a patient and to a second vascular access point, different from the first vascular access point (for example the two vascular access points can be positioned at a arteriovenous fistula).

Through the hydraulic circuit a quantity of blood is withdrawn from the first vascular access point and pumped towards the dialyzer filter.

The dialyzer filter filters said quantity of blood before it is returned to the patient in the second vascular access point through the hydraulic circuit.

If the dialyzer machine comprises said system, the light source 1 is to be installed at said dialyzer filter, so that the patient's blood is irradiated before, during or after filtering.

Below are some examples of families of microorganisms and the wavelengths (expressed in nanometers) of the light radiation used to neutralize such microorganisms.

The wavelengths were identified through a modeling of the microorganism and a simulation of the system to solve, by means of a software for numerical simulations, one or more differential equations relating to the electromagnetic field associated with the light radiation to which said microorganism is subjected.

In other words, said numerical simulations simulate the propagation of a light radiation in a 3D model of at least one microorganism belonging to a predetermined family of microorganisms, within an environment.

Each microorganism was modeled using mean values for the size.

The results of the numerical simulations are applicable to microorganisms with dimensions similar to those of the microorganisms object of the numerical simulations.

In particular, these dimensions can vary in percentage terms by a factor of ±5% with respect to the dimensions of the microorganisms subject to the numerical simulations.

Therefore, the results of the numerical simulations relating to a substantially spherical microorganism with an external diameter equal to 100 nm can be applied to microorganisms having dimensions between 95 nm and 105 nm.

The environment was modeled as a cubic volume larger than the size of the microorganism, to which the physical properties of air or water were associated, to model the behaviour of the microorganism in air or water.

In the case of modeling a virus having an external diameter equal to 100 nm, this environment can be for example a cube with dimensions equal to 800×800×800 nm³.

In the event that said microorganism is a virus, modeling its behaviour in water is particularly advantageous, since, usually, the viruses are carried within fluids, such as salivary droplets.

Figure 5:
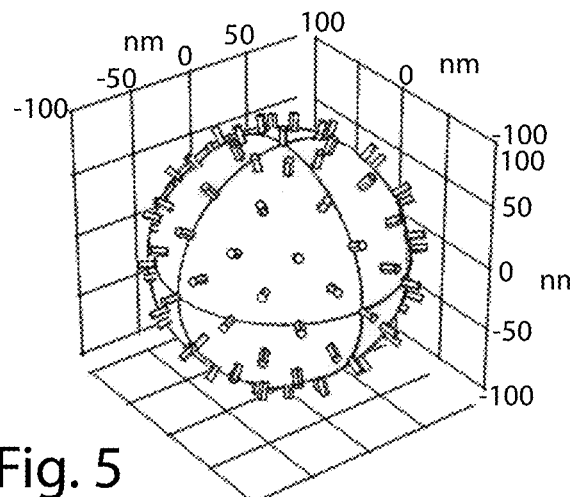
FIG. 5 is a perspective view of a virus model of the Coronaviridae family for numerical simulations.

Referring to FIG. 5B, in the case of 3D modeling of a virus belonging to the virus family called "Coronaviridiae", and in particular of SARS-COV-2, such virus was modeled using two concentric spherical elements to define four distinct regions of the virus: a first spherical element having a first diameter, and a second spherical element having a second diameter smaller than said first diameter.

In particular, the shell of said first spherical element represents a first region of the virus associated with the pericapsid and said first diameter is between 95 nm and 105 nm, and in the specific case equal to 100 nm.

The shell of said second spherical element represents a second region of the virus associated with the capsid and has a diameter between 85.5 nm and 94.5 nm and in the specific case equal to 90 nm.

In fact, it has been assumed that each shell is associated with a membrane of the microorganism and has a membrane thickness of 5 nm.

This assumption was also applied to the membrane models of further simulated viruses, better illustrated below.

A third region of the virus is between the shell of the first spherical element and the shell of the second spherical element and a fourth region of the virus is the interior of the second spherical element and is associated with the genetic material, which in this case is viral RNA.

Furthermore, the first spherical element comprises 100 protrusions, each having a length equal to 20 nm to model the spikes of the SARS-COV2.

These spikes were modeled as additional regions.

Other microorganisms can be modeled using 3D models other than the one just described. In particular, in the case of viruses comprising several membranes, the 3D model can provide a number of regions greater than the number of regions described above.

As said, the SARS-COV-2 virus has been modeled through a plurality of concentric elements having a spherical shape.

However, a microorganism can be modeled with one or more elements having an ellipsoidal shape, as explained below.

Each region of the virus has been associated with predetermined physical properties, and in particular a respective refractive index of the electromagnetic radiation.

For the SARS-COV2 virus and for all the other simulated viruses (better illustrated below), the refractive indices used are the following:

refractive index of each viral membrane: 1.1+j 0.001;
refractive index of the genetic material: 1.53+j 1.1E-7;
refractive index of the viral matrix: 1.37+j 1.1E-7; e
refractive index of the spike proteins: 1.47+j 0.00274.

The differential equations were solved by means of said software for numerical simulations.

In the embodiment being described, said software is a finite element software, in particular Comsol Multiphysics®, and more particularly Comsol Multiphysics® 5.5.

The Helmotz equation for the electromagnetic field was solved in the frequency domain or in the time domain starting from closed boundary conditions to simulate the propagation of light radiation in the microorganism inserted in said environment.

In particular, this equation has been solved in the frequency domain to reduce the calculation times necessary for processing the data obtained from the numerical simulations since the purpose of said numerical simulations is to observe the frequency behaviour of the microorganism exposed to the light radiation with a predetermined wavelength.

For each simulation, the presence of an electromagnetic field source having a predetermined wavelength and the fact that the wave was a plane wave were used as a boundary condition.

This source of electromagnetic field was placed at an infinite distance from the modeled microorganism, so as to assume that the wave front impacting this microorganism is locally flat.

In other words, the light source was placed at an infinite distance from the microorganism and emits a light radiation with said predetermined wavelength.

Furthermore, the "Perfectly Matched Layers" condition was used to model the behaviour of the external faces of the cube that represents the environment in which the microorganism is inserted.

Said condition requires a perfect absorption of the light radiations incident on said external faces of the cube with any incidence angle.

Through the aforementioned software for numerical simulations, it was possible to perform a frequency/wavelength scan of the light radiation to identify the frequency/wavelength at which the light intensity inside the microorganism has a relative maximum.

Figure 3:
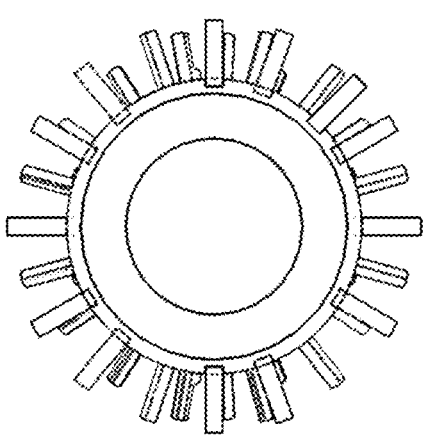
FIG. 3 is a sectional front view of a SARS-COV2 virus model for numerical simulations.

With reference to FIG. 3 and to Figures from FIG. 5 to FIG. 18, the results of the simulations carried out for viruses or bacteria belonging to the most common families are shown below.

FIGS. 3, 5, 6, 7, 8, 9, 10A, 10B, 11, 12, 13, 14, 15A, 15B, 15C, 15D, 15E, 15F, 15G, 16, 17 and 18 show a respective model of a virus or bacterium used to simulate an incident light radiation on such a virus or bacterium.

With reference to the virus family called "Corona-viridiae", a SARS COV-2 virus, shown in FIG. 3, was simulated with the characteristics already listed above.

For said virus, the following table shows the wavelength values obtained by numerical simulations at which it is possible to obtain an optical resonance, as well as a respective value obtained from the ratio between the value of the same wavelength and the value of a diameter of a single membrane with which the virus was modeled.

| Resonant wavelength λ [nm] | λ/d |
|---|---|
| 160 | 1.60 |
| 113 | 1.13 |
| 98 | 0.98 |

The possible ranges of wavelengths centred around a respective wavelength value with a bandwidth equal to 4 nm are the following:

a first wavelength range: 158 nm-162 nm, a second wavelength range: 111 nm-115 nm, a third wavelength range: 96 nm-100 nm.

In alternative embodiments, such ranges can have a bandwidth of between 1 nm and 3 nm.

The preferred wavelength value for the first wavelength range is 160 nm.

The preferred wavelength value for the second wavelength range is 113 nm.

The preferred wavelength value for the third wavelength range is 98 nm.

It is further preferable that the preferred wavelength value is 160 nm.

Each wavelength value corresponds to a peak of the simulated electromagnetic field Es (i.e. calculated by means of numerical simulations) normalized with respect to the electromagnetic input field Ein.

Figure 4:
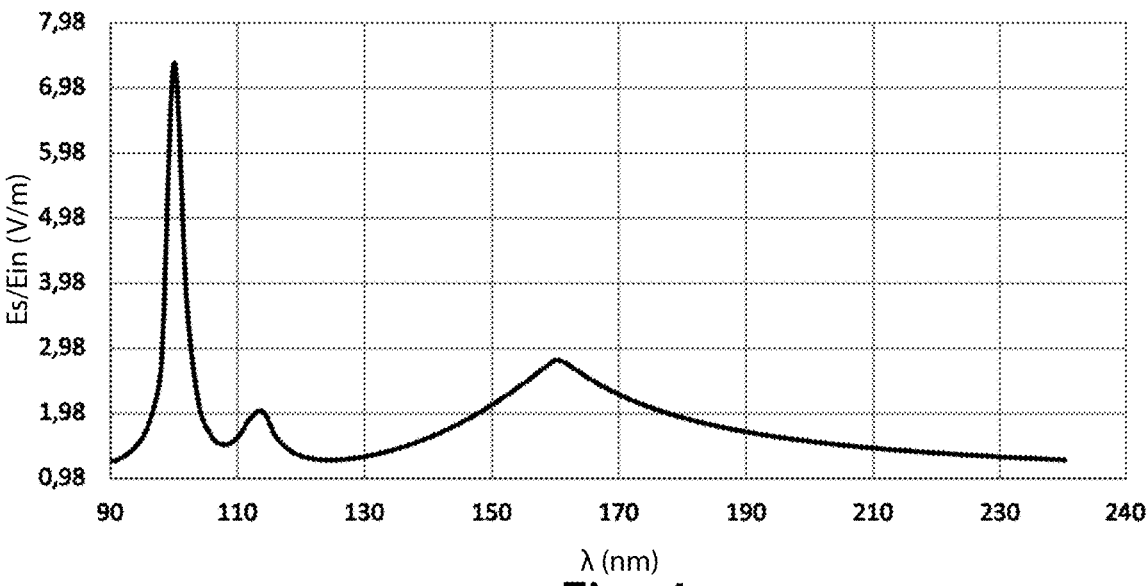
FIG. 4 shows a graph which represents a normalized electric field with respect to an input electric field, as a function of the wavelength of the light radiation emitted by the system, in which said normalized electric field has been calculated by means of a plurality finite element numerical simulations on the SARS-COV2 virus model of FIG. 3.

FIG. 4 shows a portion of the simulated electromagnetic field Es normalized with respect to the input electromagnetic field Ein with reference to the wavelengths of the visible spectrum.

The simulated electromagnetic field Es normalized in FIG. 4 has a plurality of peaks, each of which is at a respective wavelength value shown in the table shown above.

Below, for each simulated virus/bacterium with predetermined characteristics, there is a respective table showing one or more values referred to the wavelength, at which an optical resonance is obtained, as well as, for each wavelength value, at least one respective first value obtained from the ratio between the value of the same wavelength and the diameter of a first external membrane with which the virus has been modeled.

In the case of a microorganism with a membrane, d is the diameter of a spherical element representing a membrane.

In the case of a microorganism with two membranes, $d_1$ is the diameter of a first spherical element representing a first membrane or outer membrane and $d_2$ is the diameter of a second spherical element representing a second membrane, arranged in the internal volume defined by the first membrane.

Figures 6, 7, 8:
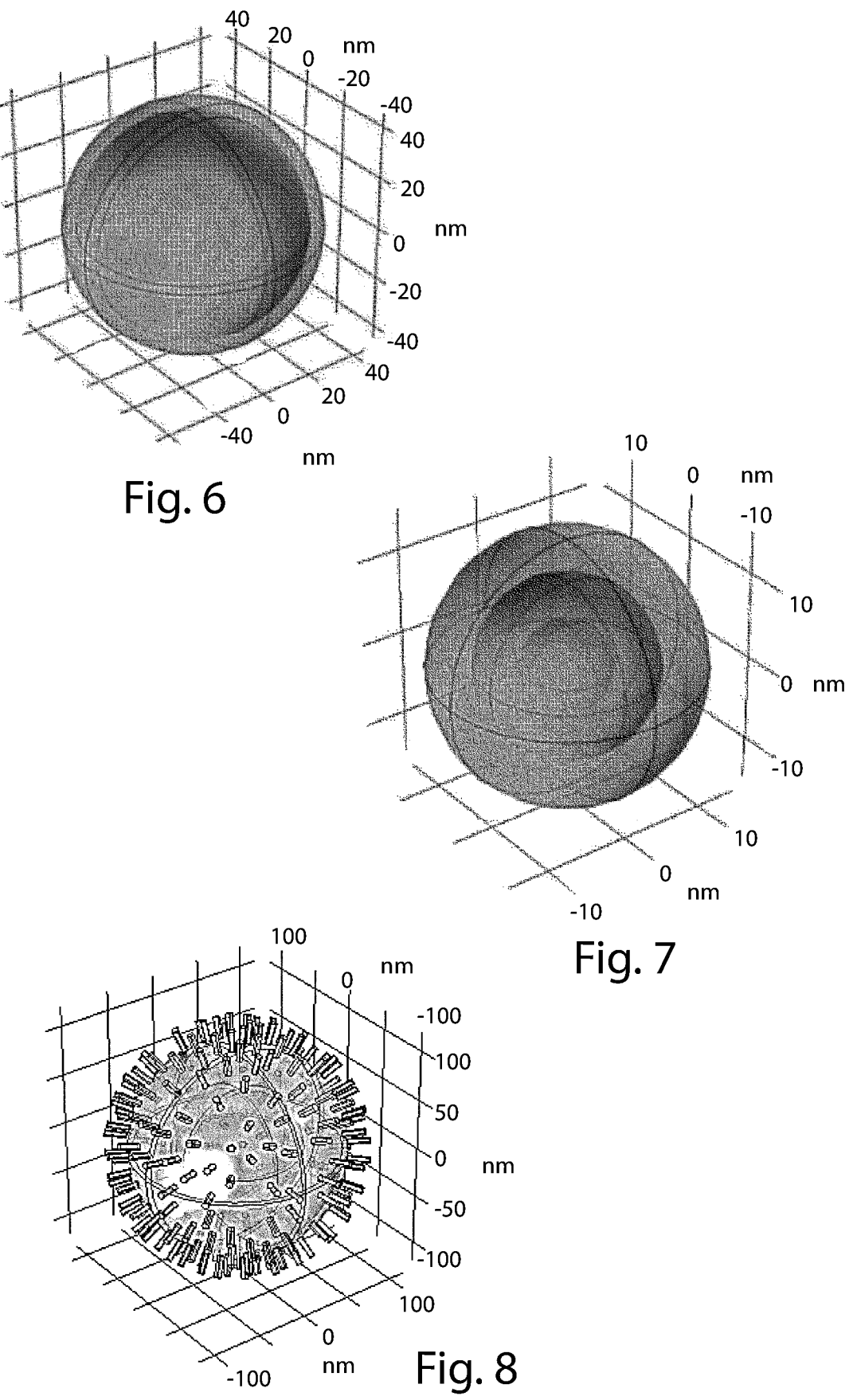
FIG. 6 is a perspective view in transparency of a rotavirus virus model for numerical simulations.
FIG. 7 is a perspective view in transparency of a virus model of the Picornavirinae family for numerical simulations.
FIG. 8 is a perspective view of a virus model of the Herpesviridae family for numerical simulations.

Still with reference to the virus family called "Corona-viridiae", a MERS or SARS-COV virus, shown in FIG. 6, has been modeled with the following characteristics:

d=diameter of a spherical element representing a membrane=180 nm, spike number=98, spike length=20 nm.

| Resonant wavelength λ [nm] | $\dfrac{\lambda}{d}$ |
|---|---|
| 174 | 0.97 |
| 136 | 0.76 |
| 128 | 0.72 |
| 102 | 0.57 |
| 86 | 0.48 |
| 74 | 0.42 |
| 58 | 0.33 |

The number of possible wavelength ranges centred around a respective wavelength value with a bandwidth equal to 4 nm are the following:

a first wavelength range: 172 nm-176 nm, a second wavelength range: 134 nm-138 nm, a third wavelength range: 126 nm-130 nm, a fourth wavelength range: 100 nm-104 nm, a fifth wavelength range: 84 nm-88 nm, a sixth wavelength range: 72 nm-76 nm, a seven wavelength range: 56 nm-60 nm.

In alternative embodiments, such ranges can have a bandwidth of between 1 nm and 3 nm.

The preferred wavelength value for the first wavelength range is 174 nm.

The preferred wavelength value for the second wavelength range is 136 nm.

The preferred wavelength value for the third wavelength range is 128 nm.

The preferred wavelength value for the fourth wavelength range is 102 nm.

The preferred wavelength value for the fifth wavelength range is 86 nm.

The preferred wavelength value for the sixth wavelength range is 74 nm.

The preferred wavelength value for the seventh wavelength range is 58 nm.

It is further preferable that the preferred wavelength value is 174 nm.

With reference to the virus family called "Reovirinae", a rotavirus virus, shown in FIG. 6, has been modeled with the following characteristics:

$d_1$=diameter of a first spherical element representing a first membrane called supercapsid=90 nm, $d_2$=diameter of a second spherical element representing a second membrane called peripcapsid=80 nm.

Furthermore, this virus has a capsid with a diameter of 30 nm.

However, the presence of the capsid was considered negligible for the modeling of the virus, as the results obtained do not change by omitting said capsid.

| Resonant wavelength λ [nm] | $\frac{\lambda}{d_1}, \frac{\lambda}{d_2}$ |
|---|---|
| 114 | 1.27, 1.425 |
| 68 | 0.76, 0.85 |
| 54 | 0.6, 0.675 |

The possible wavelengths ranges centred around a respective wavelength value with a bandwidth equal to 4 nm are the following:

a first wavelength range: 112 nm-116 nm, a second wavelength range: 66 nm-70 nm, a third wavelength range: 52 nm-56 nm.

In alternative embodiments, such ranges can have a bandwidth between 1 nm and 3 nm.

The preferred wavelength value for the first wavelength range is 114 nm.

The preferred wavelength value for the second wavelength range is 68 nm.

The preferred wavelength value for the third wavelength range is 54 nm.

It is further preferable that the preferred wavelength value is 114 nm.

With reference to the virus family called "Picornavirinae", a rhinovirus or aphthovirus or cardiovirus or hepatovirus or poliovirus, shown in FIG. 7, has been modeled with the following characteristics:

d=diameter of a spherical element associated with a membrane=30 nm.

| Resonant wavelength λ [nm] | $\frac{\lambda}{d_1}$ |
|---|---|
| 46 | 1.54 |
| 2 | 1.07 |

The possible wavelength ranges centred around a respective wavelength value with a bandwidth equal to 4 nm are the following:

a first wavelength range: 44 nm-48 nm, a second wavelength range: 30 nm-34 nm.

In alternative embodiments, such ranges can have a bandwidth between 1 nm and 3 nm.

The preferred wavelength value for the first wavelength range is 46 nm.

The preferred wavelength value for the second wavelength range is 32 nm.

It is further preferable that the preferred wavelength value is 46 nm.

With reference to the virus family called "Herpesviridae", a human cytomegalovirus virus, shown in FIG. 8, has been modeled with the following characteristics:

d=diameter of a spherical element representing a membrane=200 nm, spike number: 200, length: 20 nm.

| Resonant wavelength λ [nm] | $\frac{\lambda}{d}$ |
|---|---|
| 318 | 1.59 |
| 218 | 1.09 |
| 192 | 0.96 |
| 167 | 0.84 |

The possible wavelength ranges centred around a respective wavelength value with a bandwidth equal to 4 nm are the following:

a first wavelength range: 316 nm-320 nm, a second wavelength range: 216 nm-220 nm, a third wavelength range: 190 nm-194 nm, a fourth wavelength range: 165 nm-169 nm.

In alternative embodiments, such ranges can have a bandwidth between 1 nm and 3 nm.

The preferred wavelength value for the first wavelength range is 318 nm.

The preferred wavelength value for the second wavelength range is 218 nm.

The preferred wavelength value for the third wavelength range is 192 nm.

The preferred wavelength value for the fourth wavelength range is 167 nm.

It is further preferable that the preferred wavelength value is 318 nm.

Figures 9, 11:
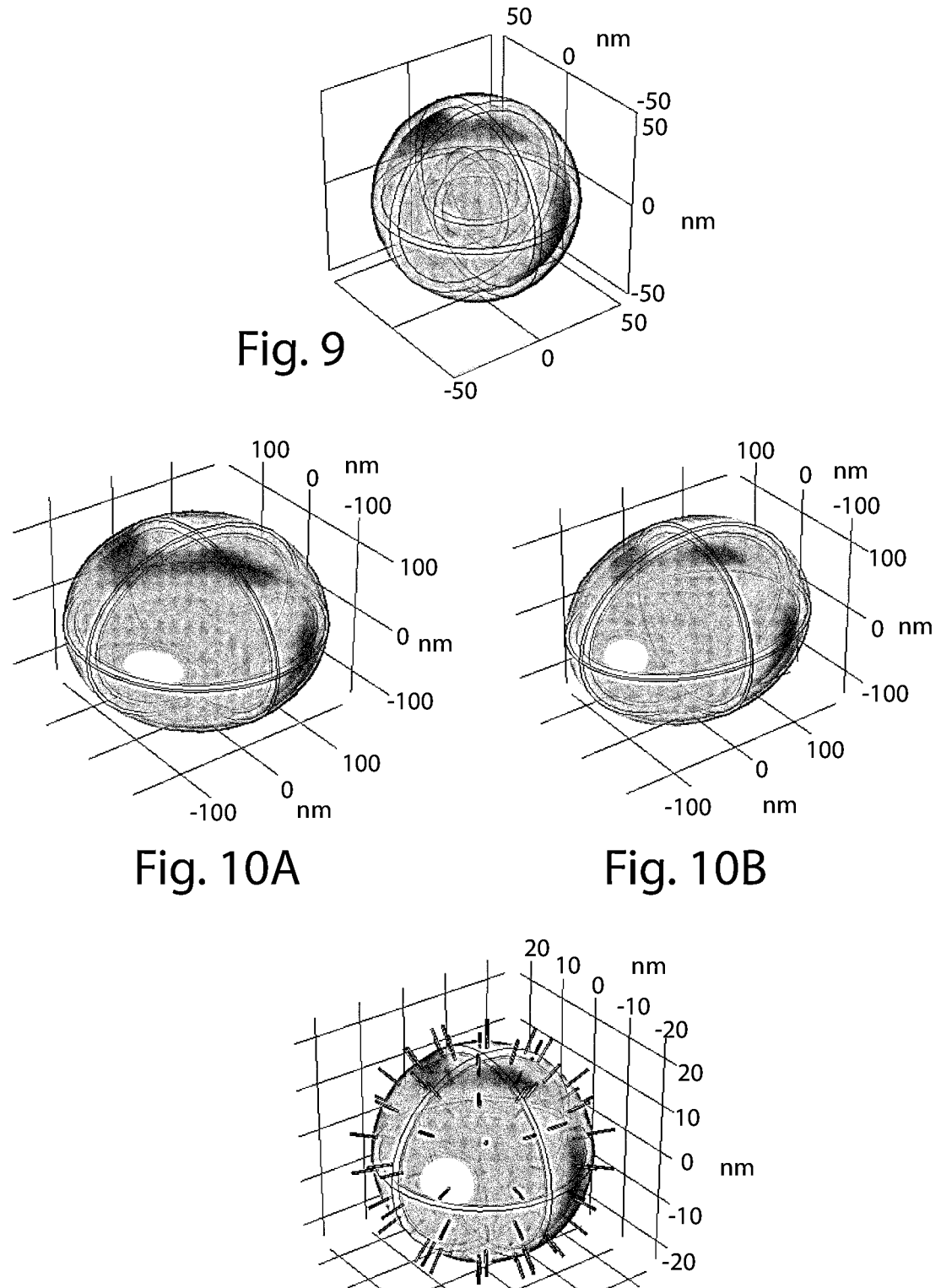
FIG. 9 is a perspective view in transparency of an HIV virus model for numerical simulations.
FIG. 11 is a perspective view of an HBV virus model for numerical simulations.

With reference to the virus family called "Retroviridae", an HIV virus, shown in FIG. 9, has been modeled with the following characteristics:

d=diameter of a spherical element representing a membrane=100 nm.

| Resonant wavelength λ [nm] | $\frac{\lambda}{d}$ |
|---|---|
| 151 | 1.51 |
| 105 | 1.05 |
| 94 | 0.94 |
| 73 | 0.73 |

The possible wavelength ranges centred around a respective wavelength value with a bandwidth equal to 4 nm are the following:

a first wavelength range: 149 nm-153 nm, a second wavelength range: 103 nm-107 nm, a third wavelength range: 92 nm-96 nm, a fourth wavelength range: 71 nm-75 nm.

In alternative embodiments, such ranges can have a bandwidth between 1 nm and 3 nm.

The preferred wavelength value for the first wavelength range is 151 nm.

The preferred wavelength value for the second wavelength range is 105 nm.

The preferred wavelength value for the third wavelength range is 94 nm.

The preferred wavelength value for the fourth wavelength range is 73 nm.

It is further preferable that the preferred wavelength value is 151 nm.

With reference to the virus family called "poxviridae", a smallpox virus, shown in FIG. 10A, has been modeled with the following characteristics:

$d_1$=the greatest diameter of a first ellipsoidal element representing a first membrane=350 nm, $d_2$=the greatest diameter of a second ellipsoidal element representing a second membrane, arranged in the internal volume defined by the first membrane=270 nm.

| Resonant wavelength λ [nm] | $\frac{\lambda}{d_1}$ | $\frac{\lambda}{d_2}$ |
|---|---|---|
| 517 | 1.48 | 1.91 |
| 347 | 0.99 | 1.29 |
| 267 | 0.76 | 0.99 |
| 216 | 0.62 | 0.80 |

The possible wavelength ranges centred around a respective wavelength value with a bandwidth equal to 4 nm are the following:

a first wavelength range: 515 nm-519 nm, a second wavelength range: 345 nm-349 nm, a third wavelength range: 265 nm-269 nm, a fourth wavelength range: 214 nm-218 nm.

In alternative embodiments, such ranges can have a bandwidth between 1 nm and 3 nm.

The preferred wavelength value for the first wavelength range is 517 nm.

The preferred wavelength value for the second wavelength range is 347 nm.

The preferred wavelength value for the third wavelength range is 267 nm.

The preferred wavelength value for the fourth wavelength range is 216 nm.

It is further preferable that the preferred wavelength value, obtained by numerical simulations, is 517 nm.

With reference to the virus family called "poxviridae", a smallpox virus shown in FIG. 10B, it has been modeled with the following additional characteristics:

$d_1$=the greatest diameter of a first ellipsoidal element representing a first membrane=320 nm $d_2$=the greatest diameter of a second ellipsoidal element representing a second membrane, arranged in the internal volume defined by the first membrane=240 nm.

| Resonant wavelength λ [nm] | $\frac{\lambda}{d_1}$ | $\frac{\lambda}{d_2}$ |
|---|---|---|
| 508 | 1.45 | 1.88 |
| 361 | 1.03 | 1.34 |
| 298 | 0.85 | 1.10 |
| 243 | 0.69 | 0.9 |
| 217 | 0.62 | 0.80 |

The possible wavelengths range centred around a respective wavelength value with a bandwidth equal to 4 nm are the following:

a first wavelength range: 506 nm-510 nm, a second wavelength range: 359 nm-363 nm, a third wavelength range: 296 nm-300 nm, a fourth wavelength range: 241 nm-245 nm, a fifth wavelength range: 215 nm-219 nm.

In alternative embodiments, such ranges can have a bandwidth between 1 nm and 3 nm.

The preferred wavelength value for the first wavelength range is 508 nm.

The preferred wavelength value for the second wavelength range is 361 nm.

The preferred wavelength value for the third wavelength range is 298 nm.

The preferred wavelength value for the fourth wavelength range is 243 nm.

The preferred wavelength value for the fourth wavelength range is 217 nm.

It is further preferable that the preferred wavelength value is 508 nm.

With reference to the virus family called "hepadnaviridae", an HBV virus (known as hepatitis B), shown in FIG. 11, has been modeled with the following additional characteristics:

d=diameter of a spherical element representing a membrane=42 nm, spike number=80, spike length=4 nm.

| Resonant wavelength λ [nm] | $\frac{\lambda}{d}$ |
|---|---|
| 69 | 1.64 |
| 40 | 0.95 |
| 31 | 0.74 |

The possible wavelength ranges centred around a respective wavelength value with a bandwidth equal to 4 nm are the following:

a first wavelength range: 67 nm-71 nm, a second wavelength range: 38 nm-42 nm, a third wavelength range: 29 nm-33 nm.

In alternative embodiments, such ranges can have a bandwidth between 1 nm and 3 nm.

The preferred wavelength value for the first wavelength range is 69 nm.

The preferred wavelength value for the second wavelength range is 40 nm.

The preferred wavelength value for the third wavelength range is 31 nm.

It is further preferable that the preferred wavelength value, obtained by numerical simulations, is 69 nm.

Figures 12, 13, 14:
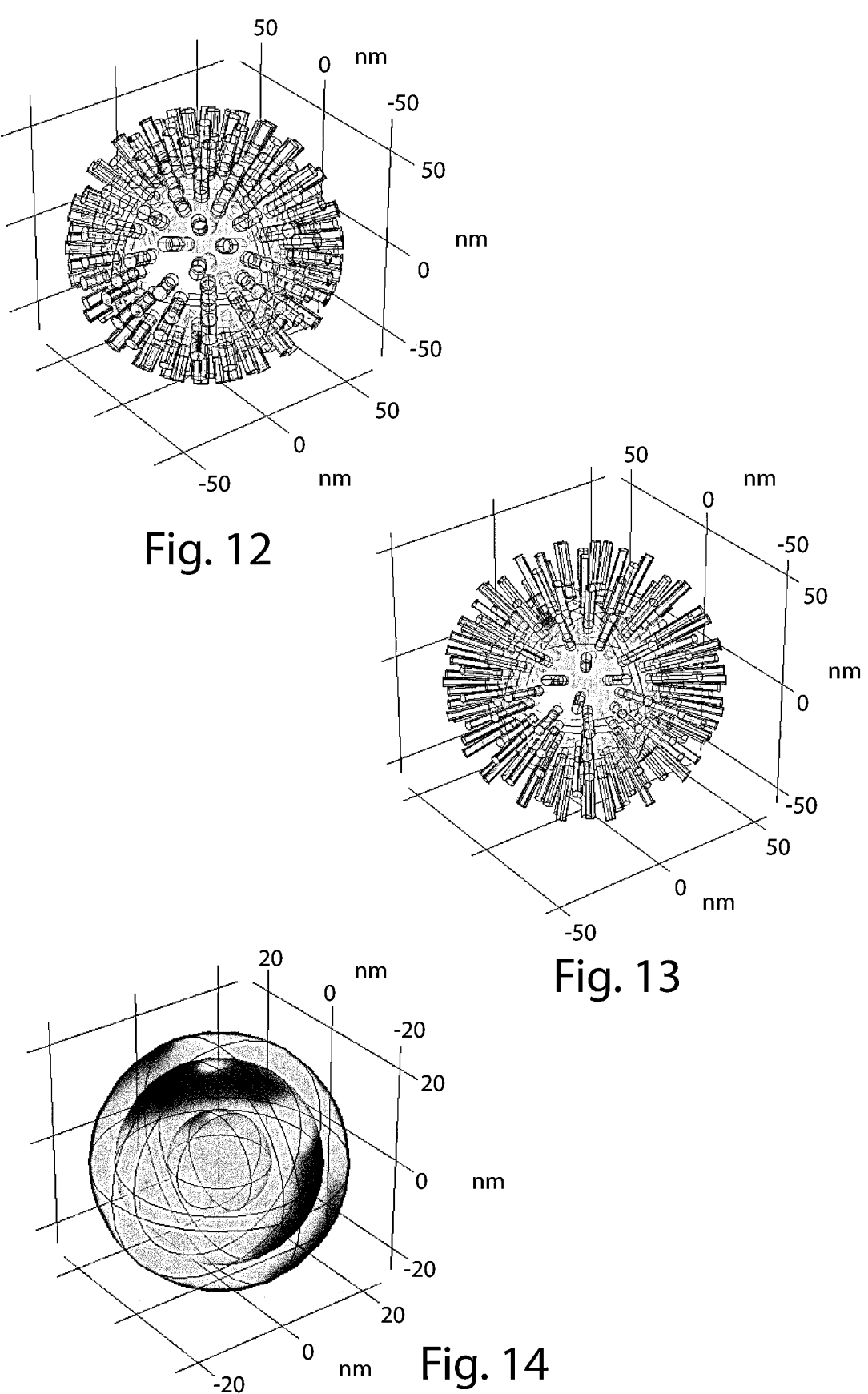
FIG. 12 is a perspective view in transparency of a virus model of the Orthomyxoviridae family for numerical simulations.
FIG. 13 is a perspective view of an Adenovirus virus model for numerical simulations.
FIG. 14 is a perspective view of an HCV virus model for numerical simulations.

With reference to the virus family called "orthomyxonaviridae", an influenza virus, shown in FIG. 12, has been modeled with the following additional characteristics:

d=diameter of a spherical element representing a membrane=110 nm, spike number=200, spike length=15 nm.

| Resonant wavelength λ [nm] | $\frac{\lambda}{d}$ |
|---|---|
| 172 | 1.56 |
| 121 | 1.10 |
| 106 | 0.96 |
| 83 | 0.75 |

The possible ranges of wavelengths centred around a respective wavelength value with a bandwidth equal to 4 nm are the following:

a first wavelength range: 170 nm-174 nm, a second wavelength range: 119 nm-123 nm, a third wavelength range: 104 nm-108 nm, a fourth wavelength range: 81 nm-85 nm.

In alternative embodiments, such ranges can have a bandwidth between 1 nm and 3 nm.

The preferred wavelength value for the first wavelength range is 172 nm.

The preferred wavelength value for the second wavelength range is 121 nm.

The preferred wavelength value for the third wavelength range is 106 nm.

The preferred wavelength value for the fourth wavelength range is 83 nm.

It is further preferable that the preferred wavelength value is 172 nm.

With reference to the virus family called "adenovirinae", an adenovirus virus shown in FIG. 13, has been modeled with the following additional characteristics:

d=diameter of a spherical element representing a membrane=80 nm, spike number=160, spike length=20 nm.

| Resonant wavelength λ [nm] | $\frac{\lambda}{d}$ |
|---|---|
| 124 | 1.55 |
| 87 | 1.09 |
| 77 | 0.96 |
| 60 | 0.75 |

The possible wavelength ranges centred around a respective wavelength value with a bandwidth equal to 4 nm are the following:

a first wavelength range: 120 nm-126 nm, a second wavelength range: 85 nm-89 nm, a third wavelength range: 75 nm-79 nm, a fifth wavelength range: 58 nm-62 nm.

In alternative embodiments, such ranges can have a bandwidth between 1 nm and 3 nm.

The preferred wavelength value for the first wavelength range is 124 nm.

The preferred wavelength value for the second wavelength range is 87 nm.

The preferred wavelength value for the third wavelength range is 77 nm.

The preferred wavelength value for the fourth wavelength range is 60 nm.

It is further preferable that the preferred wavelength value is 124 nm.

With reference to the virus family called "flaviviridae", an HCV virus (known as hepatitis C), shown in FIG. 14, has been modeled with the following additional characteristics:

d=diameter of a spherical element representing a membrane=50 nm.

| Resonant wavelength λ [nm] | $\frac{\lambda}{d}$ |
|---|---|
| 79 | 0.58 |
| 51 | 1.02 |
| 40 | 0.8 |
| 36 | 0.72 |

The possible wavelength ranges centred around a respective wavelength value with a bandwidth equal to 4 nm are the following:

a first wavelength range: 77 nm-81 nm, a second wavelength range: 49 nm-53 nm, a third wavelength range: 38 nm-42 nm, a fourth wavelength range: 34 nm-38 nm.

In alternative embodiments, such ranges can have a bandwidth between 1 nm and 3 nm.

The preferred wavelength value for the first wavelength range is 79 nm.

The preferred wavelength value for the second wavelength range is 51 nm.

The preferred wavelength value for the third wavelength range is 40 nm.

The preferred wavelength value for the fourth wavelength range is 36 nm.

It is further preferable that the preferred wavelength value is 79 nm.

Figures 15A, 15B, 15C, 15D, 15E, 15F, 15G:
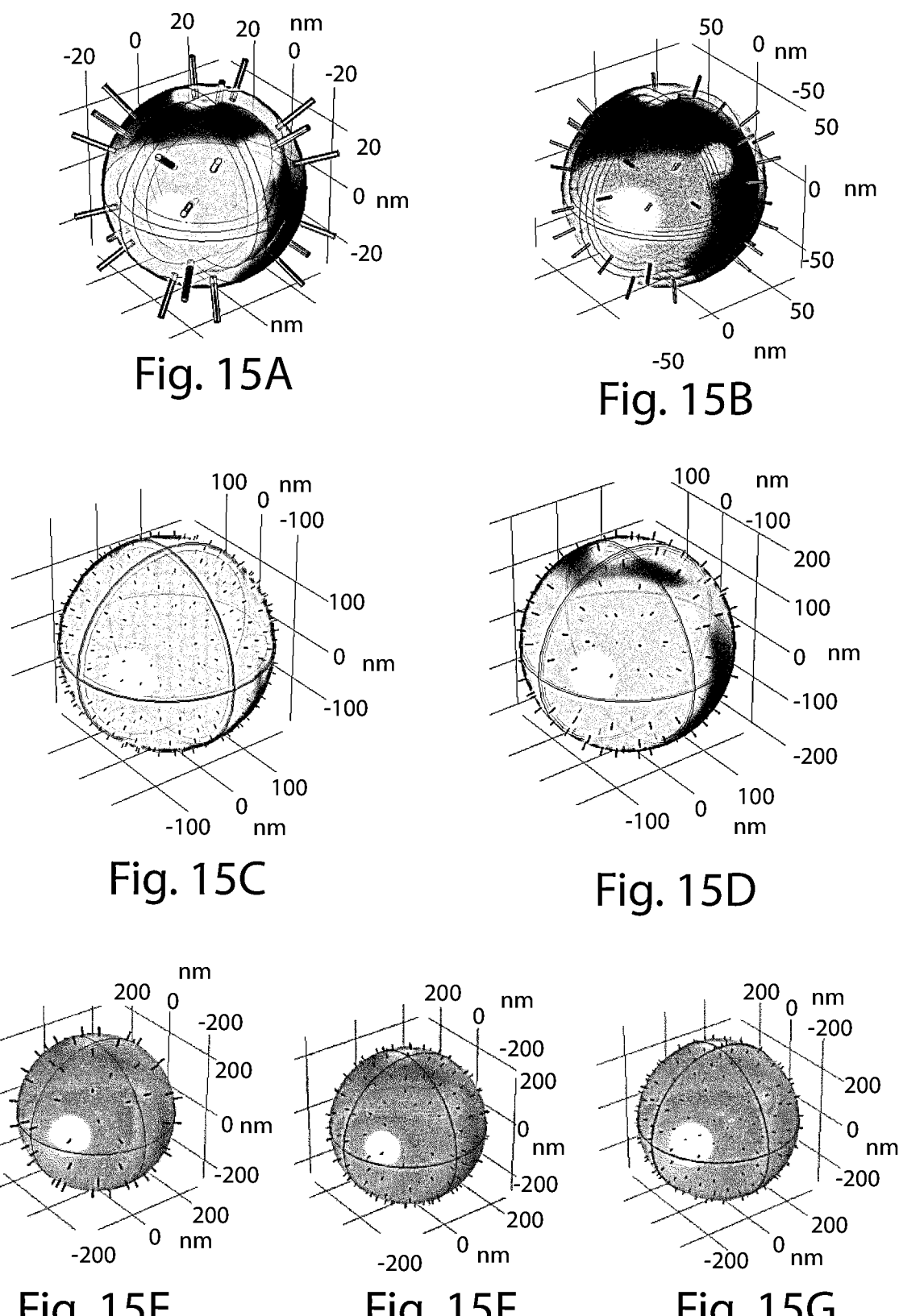
FIG. 15A is a perspective view of a first model variant of a respiratory syncytial virus RSV for numerical simulations.
FIG. 15B is a perspective view of a second model variant of a respiratory syncytial virus RSV for numerical simulations.
FIG. 15C is a perspective view of a third model variant of a respiratory syncytial virus RSV for numerical simulations.
FIG. 15D is a perspective view of a fourth model variant of a respiratory syncytial virus RSV for numerical simulations.
FIG. 15E is a perspective view of a fifth model variant of a respiratory syncytial virus RSV for numerical simulations.
FIG. 15F is a perspective view of a sixth model variant of a respiratory syncytial virus RSV for numerical simulations.
FIG. 15G is a perspective view of a seventh model variant of a respiratory syncytial virus RSV for numerical simulations.

With reference to the virus family called "paramyxoviridae" and to the subfamily called "pneumovirinae", a respiratory syncytial virus, shown in FIG. 15A, and has been modeled with the following characteristics:

d=diameter of a spherical element representing a membrane=50 nm, spike number: 22.

| Resonant wavelength λ [nm] | λ/d |
|---|---|
| 100 | 1.54 |
| 70 | 1.08 |
| 61 | 0.94 |
| 54 | 0.83 |

The possible ranges of wavelengths centred around a respective wavelength value with a bandwidth equal to 4 nm are the following:

a first wavelength range: 98 nm-102 nm, a second wavelength range: 68 nm-72 nm, a third wavelength range: 59 nm-63 nm, a fourth wavelength range: 52 nm-56 nm.

In alternative embodiments, such ranges can have a bandwidth between 1 nm and 3 nm.

The preferred wavelength value for the first wavelength range is 100 nm.

The preferred wavelength value for the second wavelength range is 70 nm.

The preferred wavelength value for the third wavelength range is 61 nm.

The preferred wavelength value for the fourth wavelength range is 54 nm.

It is further preferable that the preferred wavelength value is 100 nm.

With reference to the virus family called "paramyxoviridae" and to the subfamily called "pneumovirinae", a respiratory syncytial virus, shown in FIG. 15B, has been modeled with the following characteristics:

d=diameter of a spherical element representing a membrane=130 nm, spike number: 40.

| Resonant wavelength λ [nm] | λ/d |
|---|---|
| 200 | 1.54 |
| 140 | 1.08 |
| 122 | 0.94 |
| 108 | 0.83 |

The possible wavelength ranges centred around a respective wavelength value with a bandwidth equal to 4 nm are the following:

a first wavelength range: 198 nm-202 nm, a second wavelength range: 138 nm-142 nm, a third wavelength range: 120 nm-124 nm, a fourth wavelength range: 106 nm-110 nm.

In forme di realizzazione alternative, tali intervalli possono avere una larghezza di banda compresa tra 1 nm e 3 nm.

In alternative embodiments, such ranges can have a bandwidth between 1 nm and 3 nm.

The preferred wavelength value for the first wavelength range is 200 nm.

The preferred wavelength value for the second wavelength range is 140 nm.

The preferred wavelength value for the third wavelength range is 122 nm.

The preferred wavelength value for the fourth wavelength range is 108 nm.

It is further preferable that the preferred wavelength value is 200 nm.

With reference to the virus family called "paramyxoviridae" and to the subfamily called "pneumovirinae", a respiratory syncytial virus, shown in FIG. 15C, has been modeled with the following characteristics:

d=diameter of a spherical element representing a membrane=260 nm,
    spike number: 80.

| Resonant wavelength λ [nm] | λ/d |
|---|---|
| 406 | 1.56 |
| 287 | 1.10 |
| 245 | 0.94 |
| 222 | 0.85 |

The possible wavelength ranges centred around a respective wavelength value with a bandwidth equal to 4 nm are the following:

a first wavelength range: 404 nm-408 nm,
    a second wavelength range: 285 nm-290 nm,
    a third wavelength range: 242 nm-247 nm,
    a fourth wavelength range: 220 nm-224 nm.

In alternative embodiments, such ranges can have a bandwidth between 1 nm and 3 nm.

The preferred wavelength value for the first wavelength range is 406 nm.

The preferred wavelength value for the second wavelength range is 287 nm.

The preferred wavelength value for the third wavelength range is 245 nm.

The preferred wavelength value for the fourth wavelength range is 222 nm.

It is further preferable that the preferred wavelength value is 406 nm.

With reference to the virus family called "paramyxoviridae" and to the subfamily called "pneumovirinae", a respiratory syncytial virus, shown in FIG. 15D, has been modeled with the following characteristics:

d=diameter of a spherical element representing a membrane=390 nm,
    spike number: 120.

| Resonant wavelength λ [nm] | λ/d |
|---|---|
| 608 | 1.56 |
| 429 | 1.10 |
| 363 | 0.93 |
| 278 | 0.71 |

The possible wavelength ranges centred around a respective wavelength value with a bandwidth equal to 4 nm are the following:

a first wavelength range: 606 nm-610 nm,
    a second wavelength range: 427 nm-431 nm,
    a third wavelength range: 361 nm-365 nm,
    a fourth wavelength range: 276 nm-280 nm.

In alternative embodiments, such ranges can have a bandwidth between 1 nm and 3 nm.

The preferred wavelength value for the first wavelength range is 608 nm.

The preferred wavelength value for the second wavelength range is 429 nm.

The preferred wavelength value for the third wavelength range is 363 nm.

The preferred wavelength value for the fourth wavelength range is 278 nm.

It is further preferable that the preferred wavelength value, obtained by numerical simulations, is 608 nm.

With reference to the virus family called "paramyxoviridae" and to the subfamily called "pneumovirinae", a respiratory syncytial virus, shown in FIG. 15E, has been modeled with the following characteristics:

d=diameter of a spherical element representing a membrane=520 nm, spike number: 190.

| Resonant wavelength λ [nm] | λ/d |
|---|---|
| 816 | 1.57 |
| 578 | 1.11 |
| 492 | 0.95 |
| 450 | 0.87 |
| 380 | 0.73 |

The possible ranges of wavelengths centred around a respective wavelength value with a bandwidth equal to 4 nm are the following:

a first wavelength range: 814 nm-818 nm,
    a second wavelength range: 576 nm-580 nm,
    a third wavelength range: 490 nm-494 nm,
    a fourth wavelength range: 448 nm-452 nm,
    a fifth wavelength range: 378 nm-382 nm.

In alternative embodiments, such ranges can have a bandwidth between 1 nm and 3 nm.

The preferred wavelength value for the first wavelength range is 816 nm.

The preferred wavelength value for the second wavelength range is 578 nm.

The preferred wavelength value for the third wavelength range is 492 nm.

The preferred wavelength value for the fourth wavelength range is 450 nm.

The preferred wavelength value for the fifth wavelength range is 380 nm.

It is further preferable that the preferred wavelength value is 816 nm.

With reference to the virus family called "paramyxoviridae" and to the subfamily called "pneumovirinae", a respiratory syncytial virus, shown in FIG. 15F, has been modeled with the following characteristics:

d=diameter of a spherical element representing a membrane=650 nm, spike number: 240.

| Resonant wavelength λ [nm] | λ/d |
|---|---|
| 1019 | 1.57 |
| 723 | 1.11 |
| 616 | 0.95 |
| 562 | 0.86 |
| 476 | 0.73 |

The possible wavelength ranges centred around a respective wavelength value with a bandwidth equal to 4 nm are the following:

a first wavelength range: 1017 nm-1021 nm, a second wavelength range: 721 nm-725 nm, a third wavelength range: 614 nm-618 nm, a fourth wavelength range: 560 nm-564 nm, a fifth wavelength range: 474 nm-478 nm.

In alternative embodiments, such ranges can have a bandwidth between 1 nm and 3 nm.

The preferred wavelength value for the first wavelength range is 1019 nm.

The preferred wavelength value for the second wavelength range is 723 nm.

The preferred wavelength value for the third wavelength range is 616 nm.

The preferred wavelength value for the fourth wavelength range is 562 nm.

The preferred wavelength value for the fifth wavelength range is 476 nm.

It is further preferable that the preferred wavelength value, obtained by numerical simulations, is 1019 nm.

With reference to the virus family called "paramyxoviridae" and to the subfamily called "pneumovirinae", a respiratory syncytial virus, shown in FIG. 15F, has been modeled with the following characteristics:

d=diameter of a spherical element representing a membrane=780 nm, spike number: 280.

| Resonant wavelength $\lambda$ [nm] | $\lambda/d$ |
|---|---|
| 1224 | 1.57 |
| 868 | 1.11 |
| 742 | 0.95 |
| 570 | 0.73 |
| 530 | 068 |

The possible wavelength ranges centred around a respective wavelength value with a bandwidth equal to 4 nm are the following:

a first wavelength range: 1222 nm-1026 nm, a second wavelength range: 866 nm-870 nm, a third wavelength range: 740 nm-744 nm, a fourth wavelength range: 568 nm-572 nm, a fifth wavelength range: 528 nm-532 nm.

In alternative embodiments, such ranges can have a bandwidth between 1 nm and 3 nm.

The preferred wavelength value for the first wavelength range is 1224 nm.

The preferred wavelength value for the second wavelength range is 868 nm.

The preferred wavelength value for the third wavelength range is 742 nm.

The preferred wavelength value for the fourth wavelength range is 570 nm.

The preferred wavelength value for the fifth wavelength range is 530 nm.

It is further preferable that the preferred wavelength value, obtained by numerical simulations, is 1224 nm.

Figures 16, 17, 18:
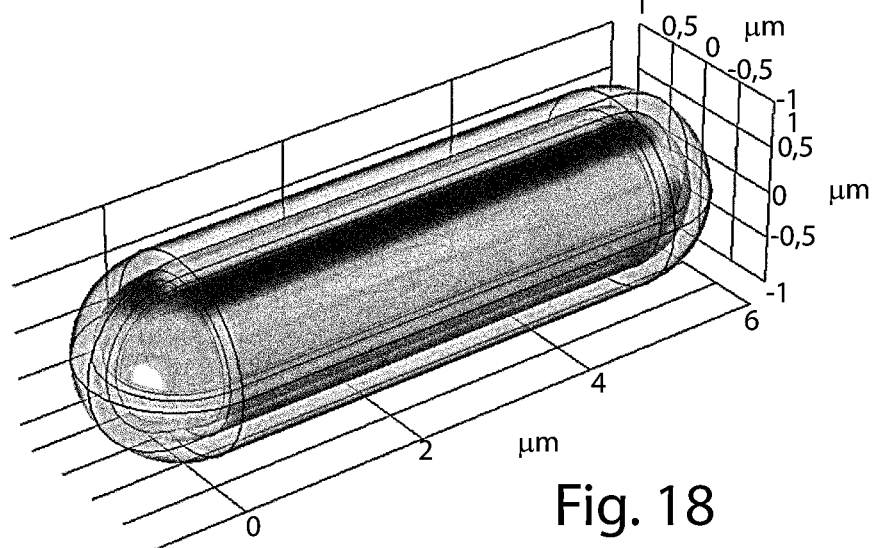
FIG. 16 is a perspective view of an *Escherichia Coli* bacterium for numerical simulations.
FIG. 17 is a perspective view of a *salmonella* bacterium for numerical simulations.
FIG. 18 is a perspective view of a *Clostridium Botulinum* bacterium for numerical simulations.

With reference to the family of bacteria called "Escherichia coli", an "Escherichia coli" bacterium, shown in FIG. 16, was modeled with the following characteristics:

$d_1$=the greatest diameter of a first ellipsoidal element representing a first membrane=3 μm, $d_2$=the greatest diameter of a second ellipsoidal element representing a second membrane, arranged in the internal volume defined by the first membrane=1 μm, flagellum number: 6, flagellum length: 3 μm.

| Resonant wavelength $\lambda$ [nm] | $\lambda/d_1$ | $\lambda/d_2$ |
|---|---|---|
| 1681 | 0.56 | 1.68 |
| 1155 | 0.39 | 1.16 |
| 1122 | 0.37 | 1.12 |
| 1088 | 0.36 | 1.09 |
| 1068 | 0.36 | 1.07 |
| 872 | 0.29 | 0.87 |
| 812 | 0.27 | 0.81 |
| 781 | 0.26 | 0.78 |
| 747 | 0.25 | 0.75 |

The possible wavelength ranges centred around a respective wavelength value with a bandwidth equal to 4 nm are the following:

a first wavelength range: 1679 nm-1683 nm, a second wavelength range: 1153 nm-1157 nm, a third wavelength range: 1120 nm-1124 nm, a fourth wavelength range: 1081 nm-1090 nm, a fifth wavelength range: 1066 nm-1070 nm, a sixth wavelength range: 870 nm-874 nm, a seven wavelength range: 810 nm-814 nm, an eighth wavelength range: 779 nm-783 nm, a ninth wavelength range: 745 nm-749 nm.

In alternative embodiments, such ranges can have a bandwidth between 1 nm and 3 nm.

The preferred wavelength value for the first wavelength range is 1681 nm.

The preferred wavelength value for the second wavelength range is 1155 nm.

The preferred wavelength value for the third wavelength range is 1122 nm.

The preferred wavelength value for the fourth wavelength range is 1088 nm.

The preferred wavelength value for the fifth wavelength range is 1068 nm.

The preferred wavelength value for the sixth wavelength range is 872 nm.

The preferred wavelength value for the seventh wavelength range is 812 nm.

The preferred wavelength value for the eighth wavelength range is 781 nm.

The preferred wavelength value for the ninth wavelength range is 747 nm.

It is further preferable that the preferred wavelength value is 1681 nm.

The data relating to simulated bacterial models are shown below. In particular, it was assumed that all bacteria have external membranes with a thickness of 50 nm and internal membranes with a thickness of 30 nm, that the refractive index for bacterial membranes is equal to 1.365+j 0.001, and that the refractive index for the cytoplasm is equal to 1.37+j 1.1E-7.

With reference to the family of bacteria called "salmonella", a salmonella bacterium, shown in FIG. 17, has been modeled with the following characteristics:

$d_1$=the greater diameter than a first ellipsoidal element representing a first membrane=2 μm, $d_2$=the greatest diameter of a second ellipsoidal element representing a second membrane, arranged in the internal volume defined by the first membrane=0.5 μm, flagellum number: 10, flagellum length: 2 μm.

| Resonant wavelength λ [nm] | $\frac{\lambda}{d_1}$ | $\frac{\lambda}{d_2}$ |
|---|---|---|
| 1149 | 0.57 | 2.30 |
| 1067 | 0.53 | 2.13 |
| 971 | 0.49 | 1.94 |
| 865 | 0.43 | 1.73 |
| 775 | 0.39 | 1.55 |
| 692 | 0.35 | 1.38 |
| 544 | 0.27 | 1.09 |

The possible wavelength ranges centred around a respective wavelength value with a bandwidth equal to 4 nm are the following:

a first wavelength range: 1147 nm-1151 nm, a second wavelength range: 1065 nm-1069 nm, a third wavelength range: 969 nm-972 nm, a fourth wavelength range: 863 nm-867 nm, a fifth wavelength range: 773 nm-777 nm, a sixth wavelength range: 690 nm-694 nm, a seven wavelength range: 543 nm-547 nm.

In alternative embodiments, such ranges can have a bandwidth between 1 nm and 3 nm.

The preferred wavelength value for the first wavelength range is 1149 nm.

The preferred wavelength value for the second wavelength range is 1067 nm.

The preferred wavelength value for the third wavelength range is 971 nm.

The preferred wavelength value for the fourth wavelength range is 865 nm.

The preferred wavelength value for the fifth wavelength range is 775 nm.

The preferred wavelength value for the sixth wavelength range is 692 nm.

The preferred wavelength value for the seventh wavelength range is 544 nm.

It is further preferable that the preferred wavelength value, obtained by numerical simulations, is 1149 nm.

With reference to the family of bacteria called "*Clostridium botulinum*", a "*Clostridium botulinum*" bacterium, shown in FIG. 18, was modeled with the following characteristics:

$d_1$=the greatest diameter of a first ellipsoidal element representing a first membrane=5 μm, $d_2$=the greatest diameter of a second ellipsoidal element representing a second membrane, arranged in the internal volume of the first membrane=1 μm.

| Resonant wavelength λ [nm] | $\frac{\lambda}{d_1}$ | $\frac{\lambda}{d_2}$ |
|---|---|---|
| 1728 | 0.35 | 1.73 |
| 1550 | 0.31 | 1.55 |
| 1420 | 0.28 | 1.42 |
| 1255 | 0.25 | 1.26 |
| 1179 | 0.23 | 1.18 |

The possible ranges of wavelengths centred around a respective wavelength value with a bandwidth equal to 4 nm are the following:

a first wavelength range: 1726 nm-1730 nm, a second wavelength range: 1548 nm-1552 nm, a third wavelength range: 1418 nm-1422 nm, a fourth wavelength range: 1253 nm-1257 nm, a fifth wavelength range: 1177 nm-1181 nm.

In alternative embodiments, such ranges can have a bandwidth between 1 nm and 3 nm.

The preferred wavelength value for the second wavelength range is 1728 nm.

The preferred wavelength value for the third wavelength range is 1550 nm.

The preferred wavelength value for the fourth wavelength range is 1420 nm.

The preferred wavelength value for the fifth wavelength range is 1179 nm.

It is further preferable that the preferred wavelength value is 1728 nm.

Advantageously, as already mentioned, through the system it is possible to neutralize a microorganism by means of a light radiation emitted by the system when in use.

A second advantage is given by the fact that, when the system is used to neutralize a microorganism present in the human body, the light radiation emitted by this system is not harmful to the health of a healthy tissue.

A further advantage is given by the fact that said system can be used to sanitize any environment or product or food or drink.

The present disclosure has been described for illustrative, but not limitative purposes, according to its preferred embodiment, but it is to be understood that variations and/or modifications can be carried out by a skilled in the art, without departing from the scope thereof, as defined according to enclosed claims.

What is claimed is:

1. A system for generating light radiation to neutralize a microorganism, said system comprising:

a light source that emits light radiation, storage media that stores:

one or more unique identification codes, each of which is associated with a respective microorganism, and at least one respective wavelength range associated with said microorganism, and a logic control unit, connected to said light source and to said storage media, and configured to:

select a wavelength range based on the microorganism to be neutralized, and activate said light source in such a way that the light radiation emitted by said light source has a wavelength within said selected wavelength range, so that, when the system is in use, said light radiation induces optical resonance in the microorganism, causing denaturation of genetic patrimony of said microorganism, wherein, when a plurality of wavelength ranges are associated with a same microorganism, said logic control unit is configured to select a corresponding wavelength range from among two or more wavelengths ranges of said plurality of wavelength ranges, in which said corresponding wavelength range has a first set of wavelength values greater than or equal to a second set of wavelength values belonging to the plurality of wavelength ranges.

2. The system according to claim 1 further comprising an optical probe.

3. The system according to claim 2, wherein said optical probe is the optical probe of a bronchoscope or a laryngopharyngeal probe or a gastroesophageal probe or an endoscopic probe.

4. The system according to claim 1, wherein said microorganism is a SARS-COV 2 virus, and wherein;

said wavelength falls within a wavelength range between 158 nm and 162 nm, said wavelength falls within a wavelength range between 111 nm and 115 nm, or said wavelength falls within a wavelength range between 96 nm and 100 nm.

5. The system according to claim 1, wherein;

said microorganism is a Mers or SARS-Cov virus, and wherein:

said wavelength falls within a wavelength range between 172 nm and 176 nm, said wavelength falls within a wavelength range between 134 nm and 138 nm, said wavelength falls within a wavelength range between 126 nm and 130 nm, said wavelength falls within a wavelength range between 100 nm and 104 nm, said wavelength falls within a wavelength range between 84 nm and 88 nm, said wavelength falls within a wavelength range between 72 nm and 76 nm, or said wavelength falls within a wavelength range between 56 nm and 60 nm.

6. The system according to claim 1, wherein:

said microorganism is a rotavirus, and wherein:

said wavelength falls within a wavelength range between 112 nm and 116 nm, said wavelength falls within a wavelength range between 66 nm and 70 nm, or said wavelength falls within a wavelength range between 52 nm and 56 nm.

7. The system according to claim 1, wherein;

said microorganism is a rhinovirus, aphthovirus, cardiovirus, hepatovirus, or a poliovirus, and wherein;

said wavelength falls within a wavelength range between 44 nm and 48 nm, or said wavelength falls within a wavelength range between 30 nm and 34 nm.

8. The system according to claim 1, wherein;

said microorganism is a human cytomegalovirus, and wherein;

said wavelength falls within a range of wavelengths between 316 nm and 320 nm, said wavelength falls within a wavelength range between 216 nm and 220 nm, said wavelength falls within a wavelength range between 190 nm and 194 nm, or said wavelength falls within a wavelength range between 165 nm and 169 nm.

9. The system according to claim 1, wherein:

said microorganism is an HIV virus, and wherein:

said wavelength falls within a wavelength range between 149 nm and 153 nm, said wavelength falls within a wavelength range between 103 nm and 107 nm, said wavelength falls within a wavelength range between 92 nm and 96 nm, or said wavelength falls within a wavelength range between 71 nm and 75 nm.

10. The system according to claim 1, wherein;

said microorganism is a smallpox virus, and the logic control unit is configured to store one or more dimensions of said smallpox virus in said storage media, and, based on a first dimension of said smallpox virus between 332.5 nm and 367.5 nm, said wavelength falls within a range of wavelengths between 515 nm and 519 nm, said wavelength falls within a wavelength range between 345 nm and 349 nm, said wavelength falls within a wavelength range between 265 nm and 269 nm, or said wavelength falls within a wavelength range between 214 nm and 218 nm, or, based on a second dimension of said smallpox virus being between 304 nm and 336 nm, said wavelength falls within a wavelength range between 506 nm and 510 nm, said wavelength falls within a wavelength range between 359 nm and 363 nm, said wavelength falls within a wavelength range between 296 nm and 300 nm, said wavelength falls within a wavelength range between 241 nm and 245 nm, or said wavelength falls within a wavelength range between 215 nm and 219 nm.

11. The system according to claim 1, wherein;

said microorganism is an HBV virus, and wherein:

said wavelength falls within a wavelength range between 67 nm and 71 nm, said wavelength falls within a wavelength range between 38 nm and 42 nm, or said wavelength falls within a wavelength range between 29 nm and 32 nm.

12. The system according to claim 1, wherein:

said microorganism is an influenza virus, and wherein;

said wavelength falls within a wavelength range between 170 nm and 174 nm, said wavelength falls within a wavelength range between 119 nm and 123 nm, said wavelength falls within a wavelength range between 104 nm and 108 nm, or said wavelength falls within a wavelength range between 81 nm and 85 nm.

13. The system according to claim 1, wherein;

said microorganism is an adenovirus, and wherein:

said wavelength falls within a wavelength range between 122 nm and 126 nm, said wavelength falls within a wavelength range between 85 nm and 89 nm, said wavelength falls within a wavelength range between 75 nm and 79 nm, or said wavelength falls within a wavelength range between 58 nm and 62 nm.

14. The system according to claim 1, wherein;

said microorganism is an HCV virus, and wherein:

said wavelength falls within a wavelength range between 77 nm and 81 nm, said wavelength falls within a wavelength range between 49 nm and 53 nm, said wavelength falls within a wavelength range between 38 nm and 42 nm, or said wavelength falls within a wavelength range between 34 nm and 38 nm.

15. The system according to claim 1, wherein:

said microorganism is a respiratory syncytial virus, and wherein, the logic control unit is configured to store one or more dimensions of said respiratory syncytial virus in said storage media, and, based on a first dimension of said respiratory syncytial virus being between 47.5 nm and 52.5 nm, said wavelength falls within a wavelength range between 98 nm and 102 nm, said wavelength falls within a wavelength range between 68 nm and 72 nm, said wavelength falls within a wavelength range between 59 nm and 63 nm, or said wavelength falls within a wavelength range between 52 nm and 56 nm; or, based on a second dimension of said respiratory syncytial virus being comprised between 123.5 nm and 136.5 nm, said wavelength falls within a wavelength range between 198 nm and 202 nm, said wavelength falls within a wavelength range between 138 nm and 142 nm, said wavelength falls within a wavelength range between 120 nm and 124 nm, or said wavelength falls within a wavelength range between 106 nm and 110 nm, or, based on a third dimension of said respiratory syncytial virus being between 247 nm and 273 nm, said wavelength falls within a wavelength range between 404 nm and 408 nm, said wavelength falls within a wavelength range between 285 nm and 289 nm, said wavelength falls within a wavelength range between 243 nm and 247 nm, or said wavelength falls within a wavelength range between 220 nm and 224 nm, or based on a fourth dimension of said respiratory syncytial virus being between 370.5 nm and 409.5 nm, said wavelength falls within a wavelength range between 606 nm and 610 nm, said wavelength falls within a wavelength range between 427 nm and 431 nm, said wavelength falls within a wavelength range between 361 nm and 365 nm, or said wavelength falls within a wavelength range between 276 nm and 280 nm, or based on a fifth dimension of said respiratory syncytial virus being between 494 nm and 546 nm, said wavelength falls within a wavelength range between 814 nm and 818 nm, said wavelength falls within a wavelength range between 576 nm and 580 nm, said wavelength falls within a wavelength range between 490 nm and 494 nm, said wavelength falls within a wavelength range between 448 nm and 452 nm, or said wavelength falls within a wavelength range between 378 nm and 382 nm, or based on a sixth dimension of said respiratory syncytial virus being between 617.5 nm and 682.5 nm, said wavelength falls within a wavelength range between 1017 nm and 1021 nm, said wavelength falls within a wavelength range between 721 nm and 725 nm, said wavelength falls within a wavelength range between 614 nm and 618 nm, said wavelength falls within a wavelength range between 560 nm and 564 nm, or said wavelength falls within a wavelength range between 474 nm and 478 nm, or based on a seventh dimension of said respiratory syncytial virus being between 741 nm and 819 nm, said wavelength falls within a wavelength range between 1222 nm and 1226 nm, said wavelength falls within a wavelength range between 866 nm and 870 nm, said wavelength falls within a wavelength range between 740 nm and 744 nm, said wavelength falls within a wavelength range between 568 nm and 572 nm, or said wavelength falls within a wavelength range between 528 nm and 532 nm.

16. The system according to claim 1, wherein:

said microorganism is an *Escherichia coli* bacterium, and wherein:

said wavelength falls within a wavelength range between 1679 nm and 1683 nm, said wavelength falls within a wavelength range between 1153 nm and 1157 nm, said wavelength falls within a wavelength range between 1120 nm and 1124 nm, said wavelength falls within a wavelength range between 1086 nm and 1090 nm, said wavelength falls within a wavelength range between 1066 nm and 1070 nm said wavelength falls within a wavelength range between 870 nm and 874 nm, said wavelength falls within a wavelength range between 810 nm and 814 nm, said wavelength falls within a wavelength range between 779 nm and 783 nm, or said wavelength falls within a wavelength range between 745 nm and 749 nm.

17. The system according to claim 1, wherein:

said microorganism is a *salmonella* bacterium, and wherein:

said wavelength falls within a wavelength range between 1147 nm and 1151 nm, said wavelength falls within a wavelength range between 1065 nm and 1069 nm, said wavelength falls within a wavelength range between 969 nm and 973 nm, said wavelength falls within a wavelength range between 863 nm and 867 nm, said wavelength falls within a wavelength range between 773 nm and 777 nm, said wavelength falls within a wavelength range between 690 nm and 694 nm, said wavelength falls within a wavelength range between 542 nm and 546 nm.

18. The system according to claim 1, wherein;

said microorganism is a *Clostridium botulinum* bacterium, and wherein:

said wavelength falls within a wavelength range between 1726 nm and 1730 nm, said wavelength falls within a wavelength range between 1548 nm and 1552 nm, said wavelength falls within a wavelength range between 1418 nm and 1422 nm, said wavelength falls within a wavelength range between 1253 nm and 1257 nm, said wavelength falls within a wavelength range between 1177 nm and 1181 nm.

19. A hemodialysis machine comprising a dialyzer filter and a hydraulic circuit that withdraws a quantity of blood from a first vascular access point and pumps said quantity of blood towards said dialyzer filter, as well as the system according to claim 1, in which said light source is arranged in correspondence with said dialyzer filter.

20. The system according to claim 1, wherein:

said light source is a UV lamp or an LED light source; and said system comprises a filter that filters said light radiation, said filter comprising a band-pass filter that filters the light radiation in such a way that said light radiation has a predetermined bandwidth less than or equal to 4 nm.

21. The system according to claim 20, wherein said system comprises an optical device arranged between said light source and said filter.

22. The system according to claim 21, wherein said optical device comprises at least one lens to decrease a diameter of the light radiation emitted by the light source or at least one diverging lens to increase the diameter of the light radiation emitted by the light source.

23. The system according to claim 20, wherein said system comprises an optical device and said filter are arranged inside said optical device.

* * * * *